United States Patent
Markson et al.

(10) Patent No.: US 11,301,630 B1
(45) Date of Patent: Apr. 12, 2022

(54) COMPUTER-IMPLEMENTED AUTOMATED AUTHORIZATION SYSTEM USING NATURAL LANGUAGE PROCESSING

(71) Applicant: Express Scripts Strategic Development, Inc., St. Louis, MO (US)

(72) Inventors: Christopher R. Markson, Hawthorne, NJ (US); Pritesh J. Shah, Paramus, NJ (US); Christopher G. Lehmuth, St. Louis, MO (US)

(73) Assignee: Express Scripts Strategic Development, Inc., St. Louis, MI (US)

( * ) Notice: Subject to any disclaimer, the term of this patent is extended or adjusted under 35 U.S.C. 154(b) by 384 days.

(21) Appl. No.: 16/575,821

(22) Filed: Sep. 19, 2019

(51) Int. Cl.
*G06F 40/284* (2020.01)
*G06N 5/00* (2006.01)
*G06F 40/253* (2020.01)

(52) U.S. Cl.
CPC .......... *G06F 40/284* (2020.01); *G06F 40/253* (2020.01); *G06N 5/003* (2013.01)

(58) Field of Classification Search
CPC .......... G06F 16/3344; G06F 40/00–58; G06N 5/003
USPC .......................... 704/1, 9, 10, 257, 270–275
See application file for complete search history.

(56) References Cited

U.S. PATENT DOCUMENTS

| | | | |
|---|---|---|---|
| 7,389,306 B2 | 6/2008 | Schuetze | |
| 7,788,096 B2 | 8/2010 | Chelba | |
| 7,813,276 B2 | 10/2010 | Gilfix | |
| 8,301,619 B2 | 10/2012 | Erhart | |
| 8,370,621 B2 | 2/2013 | Raykova | |
| 8,719,302 B2 | 5/2014 | Bailey | |
| 9,152,775 B1 * | 10/2015 | Kronrod | G06N 5/025 |
| 9,514,407 B1 * | 12/2016 | Dotan | G06N 5/022 |
| 10,216,943 B2 * | 2/2019 | Krishna | G06F 21/31 |
| 10,325,026 B2 | 6/2019 | Cardillo | |
| 10,521,572 B2 * | 12/2019 | Nygate | G06N 5/04 |
| 10,572,653 B1 * | 2/2020 | Semichev | G06N 20/00 |
| 11,023,684 B1 * | 6/2021 | Flor | G06F 40/253 |

(Continued)

OTHER PUBLICATIONS

Nikolić et al. "Attribute Selection and Intrusion Detection for Knowledge-based Authentication Systems". IASTED International Conference on Artificial Intelligence and Soft Computing 2008 at: Palma De Mallorca, Spain. Sep. 2008 (Year: 2008).*

(Continued)

*Primary Examiner* — Jesse S Pullias
(74) *Attorney, Agent, or Firm* — Miller Johnson

(57) ABSTRACT

A method includes maintaining a question repository in which each question corresponds to a set of decision trees. A distance matrix encodes a distance between each pair of questions. In response to a request for a new question, the method converts the new question into a set of tokens. For each question of the existing questions, the method determines a minimum distance between each token of the new question and the tokens of the question and sums the minimum distances to calculate a distance between the question and the new question. The method includes performing cluster analysis on the distance matrix. Performing cluster analysis includes normalizing the distance matrix and applying a hierarchical clustering process to the normalized distance matrix. Based on the cluster analysis, the method transmits an alternative question proposal or adds the new question to the question repository.

20 Claims, 9 Drawing Sheets

(56) References Cited

U.S. PATENT DOCUMENTS

| | | | |
|---|---|---|---|
| 2009/0171986 A1 | 7/2009 | Chitrapura | |
| 2009/0305670 A1* | 12/2009 | DeBoer | G10L 17/22 |
| | | | 455/411 |
| 2013/0019286 A1* | 1/2013 | Barborak | G06F 21/31 |
| | | | 726/4 |
| 2017/0236023 A1 | 8/2017 | Debnath | |
| 2018/0024981 A1* | 1/2018 | Xia | G06F 40/18 |
| | | | 715/215 |
| 2018/0218126 A1 | 8/2018 | Salazar | |
| 2019/0243900 A1* | 8/2019 | Gan | G06F 16/3329 |
| 2020/0311738 A1* | 10/2020 | Gupta | G06F 16/285 |

OTHER PUBLICATIONS

Bednarik et al. "Automated EA-type Question Generation from Annotated Texts". 7th IEEE International Symposium on Applied Computational intelligence and Informatics, May 24-26, 2012 (Year: 2012).*

Mikolov, Tomas, et al. "Efficient estimation of word representations in vector space." arXiv preprint arXiv:1301.3781 (2013).

* cited by examiner

COMPUTER-IMPLEMENTED AUTOMATED AUTHORIZATION SYSTEM USING NATURAL LANGUAGE PROCESSING

FIELD

The present disclosure relates to computer-implemented authorization systems and more particularly to automated electronic authorization systems and methods.

BACKGROUND

Many technical and business processes rely on authorization, such as authorization to access a particular technological resource, authorization to obtain a particular supply, authorization to perform a particular function, etc. These authorization systems are often administered manually, requiring a great deal of time and expertise from humans.

For example, in the context of a pharmacy benefit manager (PBM), an authorization system may be implemented to determine whether a user (sometimes referred to as a patient) is authorized by the PBM to obtain a prescription from a retail or mail-order pharmacy. The authorization may be governed by government rules, such as regulations from the Food and Drug Administration (FDA). The authorization may also be governed by guidelines provided by a drug manufacturer or distributor. Further guidelines may be promulgated by the PBM itself and by health insurers. Guidelines from health insurers may depend on the particular health plan and may diverge across different subgroups of users within a single plan. Because of the many sources of guidelines, the fact that guidelines change over time, and the fact that guidelines differ from user to user, computer automation of authorization systems has not been possible.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

An interrogatory development system includes at least one processor and a memory coupled to the at least one processor. The memory stores a question repository that includes a plurality of questions corresponding to a plurality of decision trees. Each of the plurality of questions corresponds to a set of the plurality of decision trees. The memory stores a distance matrix that encodes a distance between each pair of questions in the plurality of questions. The memory stores instructions that, upon execution, cause the at least one processor to, in response to receiving a request for a new question, convert the new question into a set of tokens. The instructions include, for each question of the plurality of questions, determining a distance between the question and the new question by (i) for each token of the new question, determining a minimum distance between the token and tokens of the question and (ii) summing the minimum distances to calculate the distance. The instructions include performing cluster analysis on the distance matrix. Performing cluster analysis includes (i) normalizing the distance matrix and (ii) applying a hierarchical clustering process to the normalized distance matrix. The instructions include, in response to the cluster analysis indicating the new question clusters with at least one of the plurality of questions, generating an alternative question proposal and transmitting the alternative question proposal as a response to the request. The instructions include, in response to the cluster analysis indicating the new question clusters with zero of the plurality of questions, adding the new question to the plurality of questions and transmitting a question added message as the response to the request.

In other features, the alternative question proposal is generated based on a selected question of the at least one of the plurality of questions. In other features, the instructions, upon execution, cause the at least one processor to assign ranks to the at least one of the plurality of questions and choose a highest-rank one of the at least one of the plurality of questions as the selected question. In other features, the ranks are based on empirical data gathered on the at least one of the plurality of questions. The empirical data indicates how frequently data can be automatically obtained for each of the at least one of the plurality of questions. In other features, the empirical data indicates how frequently automatically obtained data for each of the at least one of the plurality of questions must be modified.

In other features, the instructions, upon execution, cause the at least one processor to incorporate the distances between the questions and the new question into the distance matrix. In other features, determining a first minimum distance between a first token and tokens of the question includes determining a set of distances and selecting a smallest one of the set of distances as the first minimum distance. Each distance of the set of distances indicates distance between a vector representation of the first token and a vector representation of a respective token of the question.

In other features, a distance between the vector representation of the first token and a vector representation of a second token is calculated as a Euclidean distance between the vector representation of the first token and the vector representation of the second token. In other features, the memory stores a vector data store including a plurality of vector representations. Each vector representation of the plurality of vector representations corresponds to a respective token.

In other features, converting the new question into a set of tokens includes performing word stemming on words in the new question, removing punctuation from the new question, and selectively removing words from the new question. Each token of the set of tokens corresponds to a remaining word of the new question. In other features, a word list specifies words to be removed from the new question and the word list includes medical terms. In other features, the medical terms includes brand names of prescription drugs and generic names of prescription drugs. In other features, the hierarchical clustering process includes k-means clustering.

A method includes maintaining a question repository that includes a plurality of questions corresponding to a plurality of decision trees. Each of the plurality of questions corresponds to a set of the plurality of decision trees. The method includes maintaining a distance matrix that encodes a distance between each pair of questions in the plurality of questions. The method includes, in response to receiving a request for a new question, converting the new question into a set of tokens. The method includes, for each question of the plurality of questions, determining a distance between the question and the new question by (i) for each token of the new question, determining a minimum distance between the token and tokens of the question and (ii) summing the minimum distances to calculate the distance. The method includes performing cluster analysis on the distance matrix. Performing cluster analysis includes (i) normalizing the distance matrix and (ii) applying a hierarchical clustering process to the normalized distance matrix. The method includes, in response to the cluster analysis indicating the new question clusters with at least one of the plurality of questions, generating an alternative question proposal and transmitting the alternative question proposal as a response to the request. The method includes, in response to the cluster analysis indicating the new question clusters with zero of the plurality of questions, adding the new question to the plurality of questions and transmitting a question added message as the response to the request.

In other features, the alternative question proposal is generated based on a selected question of the at least one of the plurality of questions. In other features, the method includes assigning ranks to the at least one of the plurality of questions and choosing a highest-rank one of the at least one of the plurality of questions as the selected question. In other features, the ranks are based on empirical data gathered on the at least one of the plurality of questions. The empirical data indicates how frequently data can be automatically obtained for each of the at least one of the plurality of questions. The empirical data indicates how frequently automatically obtained data for each of the at least one of the plurality of questions must be modified.

In other features, the method includes incorporating the distances between the questions and the new question into the distance matrix. In other features, determining a first minimum distance between a first token and tokens of the question includes determining a set of distances and selecting a smallest one of the set of distances as the first minimum distance. Each distance of the set of distances indicates Euclidean distance between a vector representation of the first token and a vector representation of a respective token of the question. In other features, converting the new question into a set of tokens includes performing word stemming on words in the new question, removing punctuation from the new question, and selectively removing words from the new question. Each token of the set of tokens corresponds to a remaining word of the new question.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Figure 1:
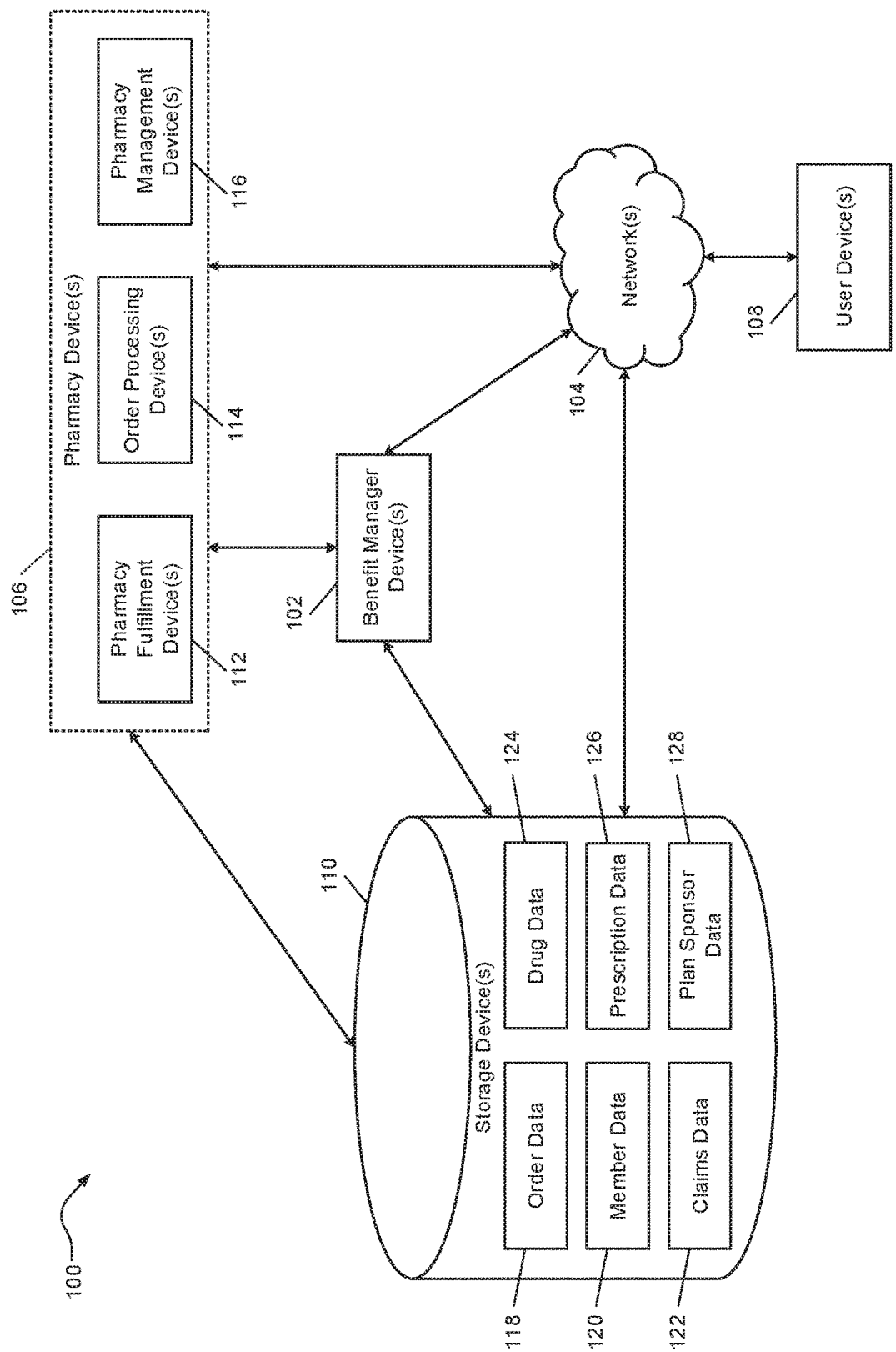
FIG. 1 is a functional block diagram of an example system including a high-volume pharmacy.

Authorization systems may rely on a hierarchical decision tree to determine whether a particular service, access right, or prescription is authorized. To assess whether a particular item is authorized, the hierarchical tree is traversed from a root node to one of the leaf nodes at which decisions are located. In some cases, the decision is binary, such as approval or denial. In other cases, the decision may have additional nuance, such as an approval but with a caveat. The caveat may include the need for an additional action on the part of the requesting user or for an additional monetary contribution by the requesting user.

Traversing the tree may require answering a question at each node to determine which branch of the tree to take. Each question may solicit information about the requesting user, such as their role in an organization or their blood type. Creation of these hierarchical decision trees may be performed by humans who assess the relevant regulations, requirements, guidelines, etc. to determine what questions must be asked to determine authorization.

These questions may vary widely, even when the information sought is similar or the same. For example, when assessing whether a particular item is authorized, a question in the decision tree may ask the age of the user; for the decision tree of another authorization, a question may ask how old the user is. Of course, much more sophisticated variations on this also exist. As a contextual example, a set of decision trees for pharmaceutical authorizations may encompass 30,000 separate questions. For complex authorization schemes, attempting to standardize, normalize, or harmonize the questions is not feasible for humans to do and, absent the present disclosure, is not simply a computational problem implementable on a computer.

The present disclosure describes improvements to authorization systems that allow for authorization processes to be increasingly electronic and automated. For example, in the context of prior authorization of a prescription written to a user, a prior authorization operator may need to answer a series of questions regarding the user. The operator may include one or more of the following people: a clinician (such as a doctor, physician assistant, or nurse), a staff member in the clinician's office, a pharmacist, a PBM employee, a health plan employee, etc.

In various implementations, for a particular authorization, the operator may be presented with all of the potentially relevant questions for that authorization. In a pharmaceutical example, even though LDL cholesterol may be irrelevant for a user below a certain age, the questions posed may gather all the information necessary to traverse any branch of the tree, including both age and LDL cholesterol. In this way, the questions posed do not rely on the structure of the hierarchical decision tree but instead only rely on the list of relevant questions.

In other implementations, the questions posed may be limited to those questions that are relevant to traversing a single path of the hierarchical decision tree for the particular user. This requires the questions to be posed serially, with each answer potentially changing what the next question will be.

According to the present disclosure, questions across some or all decision trees can be clustered and normalized to allow answers to be obtained in an automated fashion by the computer-implemented system. For example, once a cluster of questions related to the user's age is identified, the age can be retrieved for that user from an electronic health records (EHR) system. This retrieved answer may immediately be used to traverse the hierarchical decision tree and arrive at the next question or at an authorization decision. Alternatively, the retrieved answer may be displayed to a verifier before proceeding to the next node of the decision tree. The verifier may be the same person as or different than the operator. In various implementations, some verifiers may verify different types of answers and in some cases multiple verifiers may verify the same piece of information.

In one example, an automated system may, without operator input beyond selecting the prior authorization desired and specifying the relevant user, retrieve answers that allow traversal of the hierarchical decision tree to arrive at an approval or denial. This set of answers may be displayed to the operator or verifier to verify the accuracy of the answers. In some cases, rules or guidelines may require that the verifier be the prescribing clinician (the clinician who "wrote" the prescription). The answers may be displayed along with source material such as electronic health records (EHR) or electronic medical records (EMR) to demonstrate the context from which the answer was obtained.

In some implementations, the authorization result may be displayed at the time of verification. In other implementations, the authorization result may be hidden to reduce the temptation of adjusting answers to arrive at a particular decision. Once the answers are verified, the adjudication result is established. The authorization result may be subject to appeal or review. The appeals process may also rely on various questions, which may be clustered and normalized according to the present disclosure. Further, another hierarchical decision tree may be used as an input (or as the sole basis) for the appeals process.

In another example implementation of an adjudication process, an operator (in the prescription context, this might be the prescribing clinician or their office manager or insurance specialist) may be presented serially with questions used in determining an authorization result. As each question is presented, an answer is provided automatically for approval by the operator. As appropriate, the operator either approves or adjusts the answer. The answer, as adjusted, is then used to traverse the hierarchical decision tree and either come to a decision or arrive at another question.

Automating this authorization process can dramatically improve the speed of authorization decisions. Not only is less human effort required, but the decision will arrive fast enough that corrective action can be taken more effectively. For example, if a clinician identifies that an authorization will be denied soon after meeting with the user, the clinician may consider an alternative treatment option with the relevant information still fresh in memory. By automating the authorization process, the clinician or a member of the clinician's staff can perform at least a preliminary authorization while the user receiving the prescription is still present. Otherwise, a follow-up visit may need to be scheduled and attended. Such delays and additional visits are not only costly in terms of time and resources; they can decrease the likelihood of the user receiving effective treatment and can delay effective treatment. As a result, users may experience gaps in care, especially for users who, after an authorization denial, do not immediately follow up with their clinical provider.

The much greater speed of authorization allowed by the present disclosure also enables rapid identification of incorrect health information. Traditionally, a user may receive an authorization denial, attempt to understand the basis for the denial, and only then recognize that incorrect medical information is present (a process that may take weeks or even months). According to the present disclosure, the automated system allows the operator to immediately correct or initiate steps toward correcting the erroneous information.

Clustering

The present disclosure describes how questions related to the authorization process can be clustered according to semantic similarity. This can be used to harmonize sets of existing questions and can also be used to identify existing questions when a new question is proposed for an authorization decision tree. Each existing question corresponds to (that is, will determine at least one decision) in a set of decision trees. An existing question may no longer be in use and therefore the set of decision trees corresponding to the existing question would be the empty set.

For example, if a clinical team is developing (or updating) a decision tree for a particular authorization, the clinical team may prepare a new question to be asked for purposes of the authorization. The new question can be compared to the entire set of existing questions. First, a vector of distances between the new question and each existing question is generated. In various implementations, this vector may be maintained for every question added to the set to create a distance matrix, with each vector in the distance matrix identifying the distances between a given question and the rest of the questions in the set. This distance matrix can then be used to cluster the questions. While described in detail below, one example of a clustering process is k-means clustering.

In various implementations, a new question can be added to the set of existing questions and a clustering analysis performed on the resulting combined set. In other implementations, the system identifies which (if any) of the clusters from the set of existing questions the new question falls into.

If the new question ends up in a cluster with other questions, an operator of the authorization system may evaluate whether the new question is duplicative of one of the existing questions. If so, one of the existing questions may be used for the decision tree rather than the proposed new question.

When a new question falls into a cluster occupied by one or more existing questions, the system may select one or more of the existing questions for presentation to the operator. The operator may then assess whether one of the existing questions can be used to elicit the same or similar information for purposes of traversing the hierarchical decision tree.

During operation of the authorization process, the system may track the performance of each question in the question repository. For example, the system may track how often data can automatically be obtained for a particular question. In addition, the system may track how often an operator needs to change data automatically obtained for the question. Further, the system may track how often data is unavailable or not provided for a question. The questions within a cluster may be ranked, with those questions that are more frequently able to be automatically and accurately answered receiving a higher ranking. The system may then present the highest-ranked question from the cluster as an alternative to a proposed new question.

The present disclosure also describes converting a legacy set of manually-created questions into a set of clustered questions. According to one approach, a new empty set of questions is created and a first question from the legacy set is added to the new set. Then the second question from the legacy set is proposed as a new question with respect to the new set of questions according to the principles described below. The remaining questions from the legacy set of questions are then processed one at a time until all of the questions are processed and the new set of questions is complete. In various implementations, questions that are redundant (that is, having a sufficiently small distance to already-added questions) may be excluded as duplicates or may be retained. When multiple questions with a short distance between them are retained, one may be selected as the preferred alternative for the question based on efficacy data.

In more detail, the distance between two questions may be based on a processed and tokenized form of the questions. For example, a first token of a first question may be compared against all of the tokens of the second question. The minimum distance between the first token and any token of the second question is recorded. This is repeated for each of the tokens in the first question. The distance between the two questions may then be calculated based on a sum of the minimum distances for each of the tokens of the first question.

The distance between one token and another token may be determined as a Euclidean distance between vector representations of the tokens. The Euclidean distance between two n-dimensional vectors is the square root of the sum of n squares. The nth square is the square of the difference between the nth element of the first vector and the nth element of the second vector. In various implementations, the square root may be omitted from all calculations to reduce processing overhead.

The vector representation of a token may be retrieved from a dictionary. In various implementations, the dictionary may be built from or directly access a machine-learning model. The machine-learning model may be trained on medical documents to build up an n-dimensional vector representation of each token in the documents. As with many machine-learned models, each position in the n-dimensional vector may not have any human-recognizable semantic meaning. For example only, see T. Miolov, Efficient Estimation of Word Representations in Vector Space, Sep. 7, 2013, arXiv:1301.3781, the entire disclosure of which is incorporated by reference.

If there is an ontological match between a first token of the first question and any of the tokens of the second question, the distance recorded for the first token may be set to a minimum value such as zero. An ontology allows an administrator of the authorization system to manually identify terms that are used interchangeably in questions relevant to the authorization system, and prevent interchangeable terms from being inaccurately understood as having a greater distance between them.

Another gloss on distance determination is the identification of sensitive terms. A sensitive term is a token that may have substantively different semantic meanings. The term is therefore ambiguous and any vector representation of the term may not be reliable for distance calculation. In various implementations, the distance used for a sensitive term token may be set to a predetermined nonzero value. The set of sensitive terms may be established by one or both of the machine-learning model (for example, through recognition that the semantic value of a term is not converging) and human curation.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
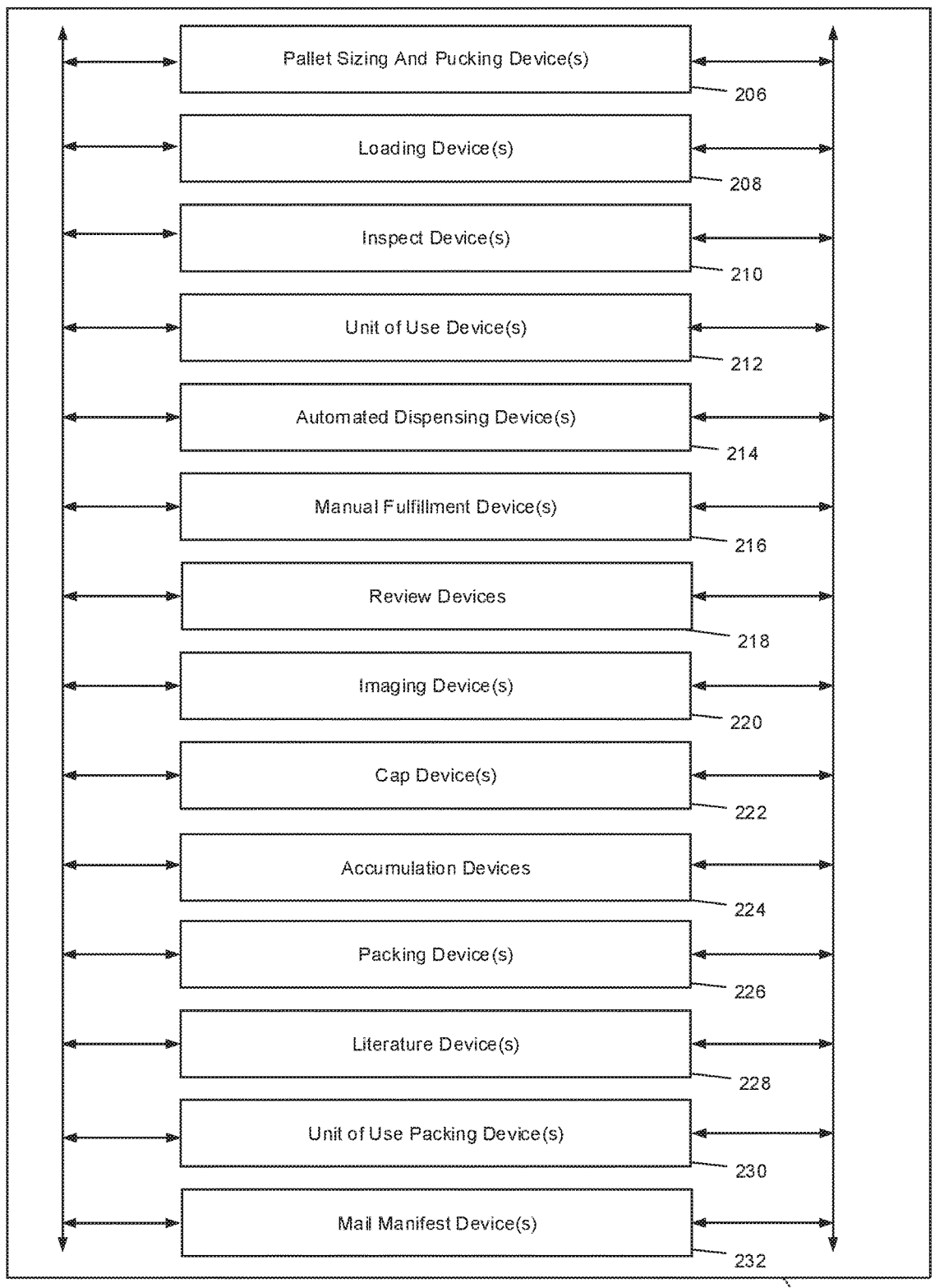
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
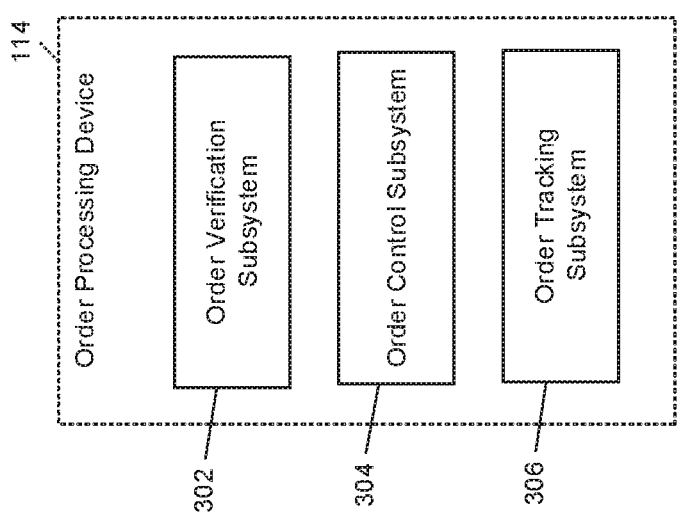
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Block Diagram

Figure 4:
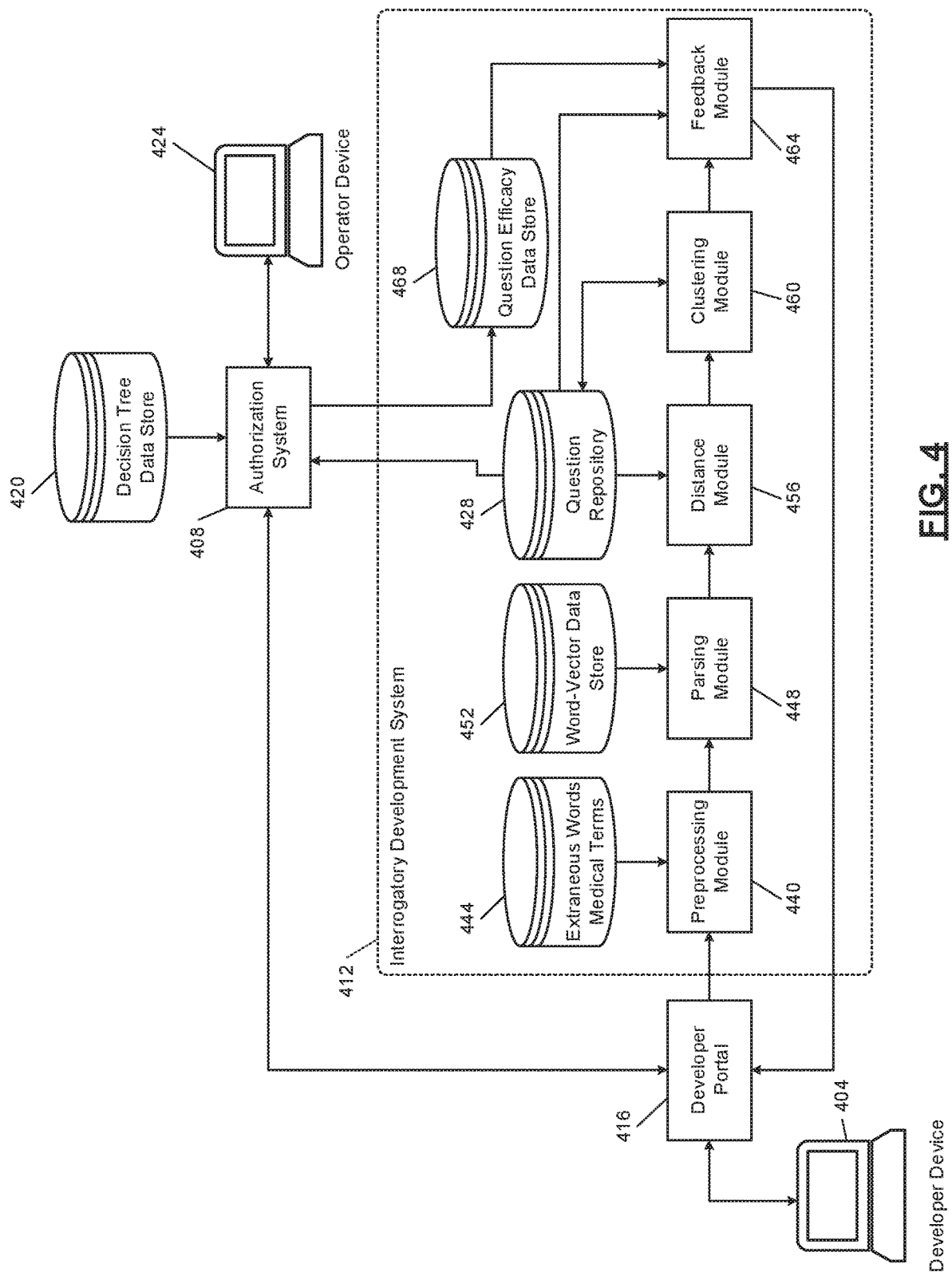
FIG. 4 is a block diagram of an environment including an example interrogatory development system.

In FIG. 4, a developer using a developer device 404 accesses an authorization system 408 and an interrogatory development system 412. The developer may access the authorization system 408 and the interrogatory development system 412 using a developer portal 416, which may be implemented as a website hosted on a web server. Using the developer portal 416, the developer can develop hierarchical decision trees for processing prior authorizations.

The authorization system 408 stores these decision trees in a decision tree data store 420. A decision tree from the decision tree data store 420 may be processed by the authorization system 408 to determine a prior authorization for a particular user's prescription. An operator accesses the authorization system 408 using an operator device 424. For example, the operator may be a clinician or a staff member working for a clinician. The operator can conduct a prior authorization check using the authorization system 408 to determine whether a user can be prescribed a particular medication. The operator may perform this prior authorization while the user is present, such as during or after a clinician appointment.

The authorization system 408 may be guided in the authorization process by a decision tree from the decision tree data store 420. The decision tree is traversed by asking a question for each node, the answer to which will indicate which branch of the tree should be followed. These questions may be obtained from a question repository 428, which is shown as part of the interrogatory development system 412 but may be stored elsewhere, such as with the decision tree data store 420.

The developer develops decision trees based on governmental guidelines, such as state guidelines and federal guidelines from the Food and Drug Administration (FDA). The decision tree may vary based on the particular health plan due to different requirements established by health plan providers/insurers. When the developer needs to prepare a new question for making a decision as part of a decision tree, the developer uses the developer portal 416 to submit the question to the interrogatory development system 412.

In the interrogatory development system 412, the question is transformed by a preprocessing module 440, which may rely on a dictionary 444 of extraneous terms and medical terms. The transformed question is parsed by a parsing module 448, which parses the transformed question into a set of tokens. Then, each token is represented by a vector from a word-vector data store 452. The word-vector data store 452 may be generated by a machine-learning model that has been trained with medical documents.

The parsed question is provided to a distance module 456, which maintains a distance matrix describing the distance between each question in the question repository 428. The distance module 456 determines the distance between the parsed question and every current question in the question repository 428. The distance module 456 may rely on an ontology from an ontology data store (not shown).

A clustering module 460 uses the distance matrix from the distance module 456 to cluster questions in the question repository 428 into a set of clusters. A feedback module 464 assesses how the new question from the developer portal 416 fits with existing clusters. Feedback on the new question is then returned to the developer portal 416.

The feedback module 464 may identify whether the new question is similar to existing questions, such as when the new question falls into a cluster with existing questions. If so, the feedback module 464 may suggest to the developer portal 416 that the developer use one of the existing questions instead of adding the new question. The feedback module 464 may select one or more proposed alternatives from the question repository 428 based on data in a question efficacy data store 468.

During operation of the authorization system 408, data concerning whether answers are obtained for questions is recorded in the question efficacy data store 468. The question efficacy data store 468 may include information about how frequently automated answers are able to be obtained for each question and also how frequently automated answers are corrected, such as by the operator, an indication that the obtained data may not be reliable. If the new question is added to the question repository 428, the developer can use the new question in a decision tree (which will be stored in the decision tree data store 420).

The developer portal 416, the authorization system 408, and the interrogatory development system 412 may be implemented by the benefit manager device 102 of FIG. 1. The question repository 428 and the decision tree data store 420 may be stored by the storage device 110 of FIG. 1. The developer device 404 and the operator device 424 may be instances of the user device 108 of FIG. 1.

Flowcharts

Figure 5:
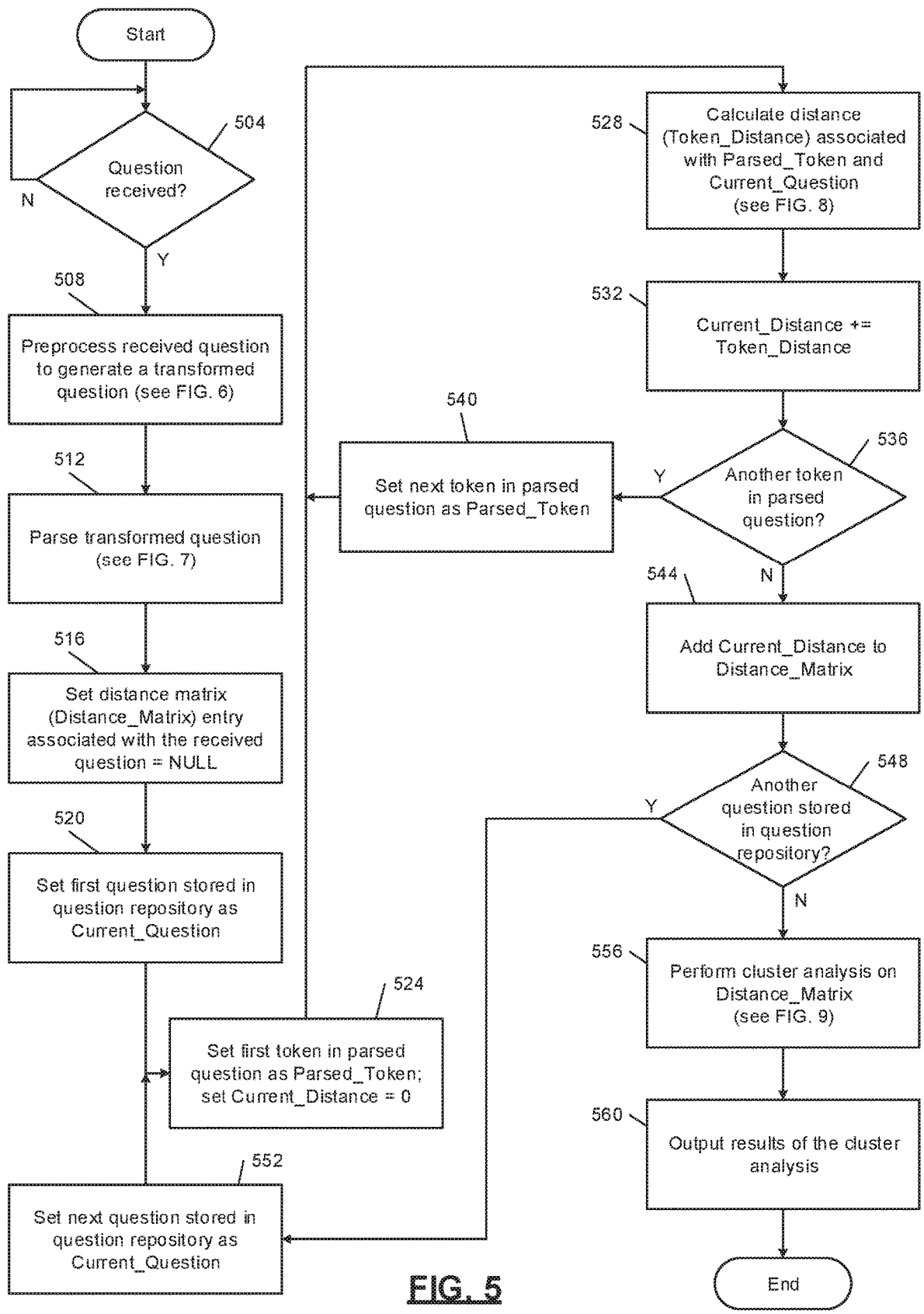
FIG. 5 is a flowchart of an example process for interrogatory development.

In FIG. 5, an example process for interrogatory development is described. For example, the process may be implemented by the interrogatory development system 412 of FIG. 4. Control in FIG. 5 begins at 504. In various implementations, as soon as the control of FIG. 5 ends, control may restart back at 504. This allows control to process multiple questions in series. In various implementations, question processing may be parallelized such that two or more questions can be processed in partially or wholly overlapping timeframes.

Figure 6:
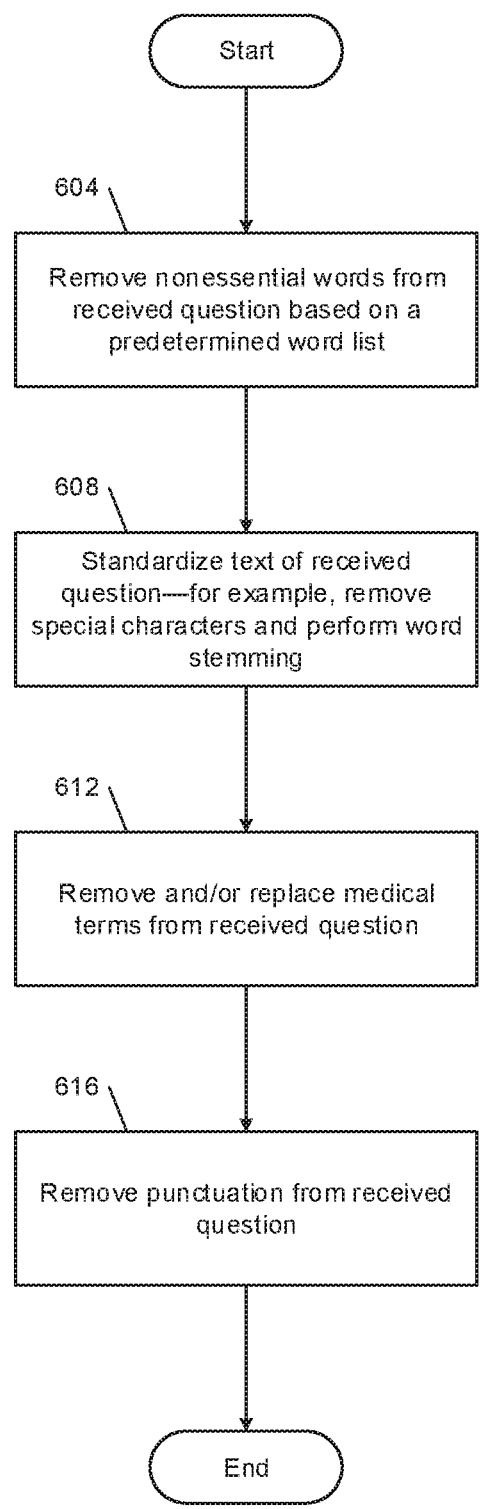
FIG. 6 is a flowchart of an example question preprocessing method.

At 504, control determines whether a question has been received, such as from a developer portal. If so, control transfers to 508; otherwise, control remains at 504. At 508, control preprocesses the received question to generate a transformed question. In various implementations, this preprocessing may be performed as shown in FIG. 6.

Figure 7:
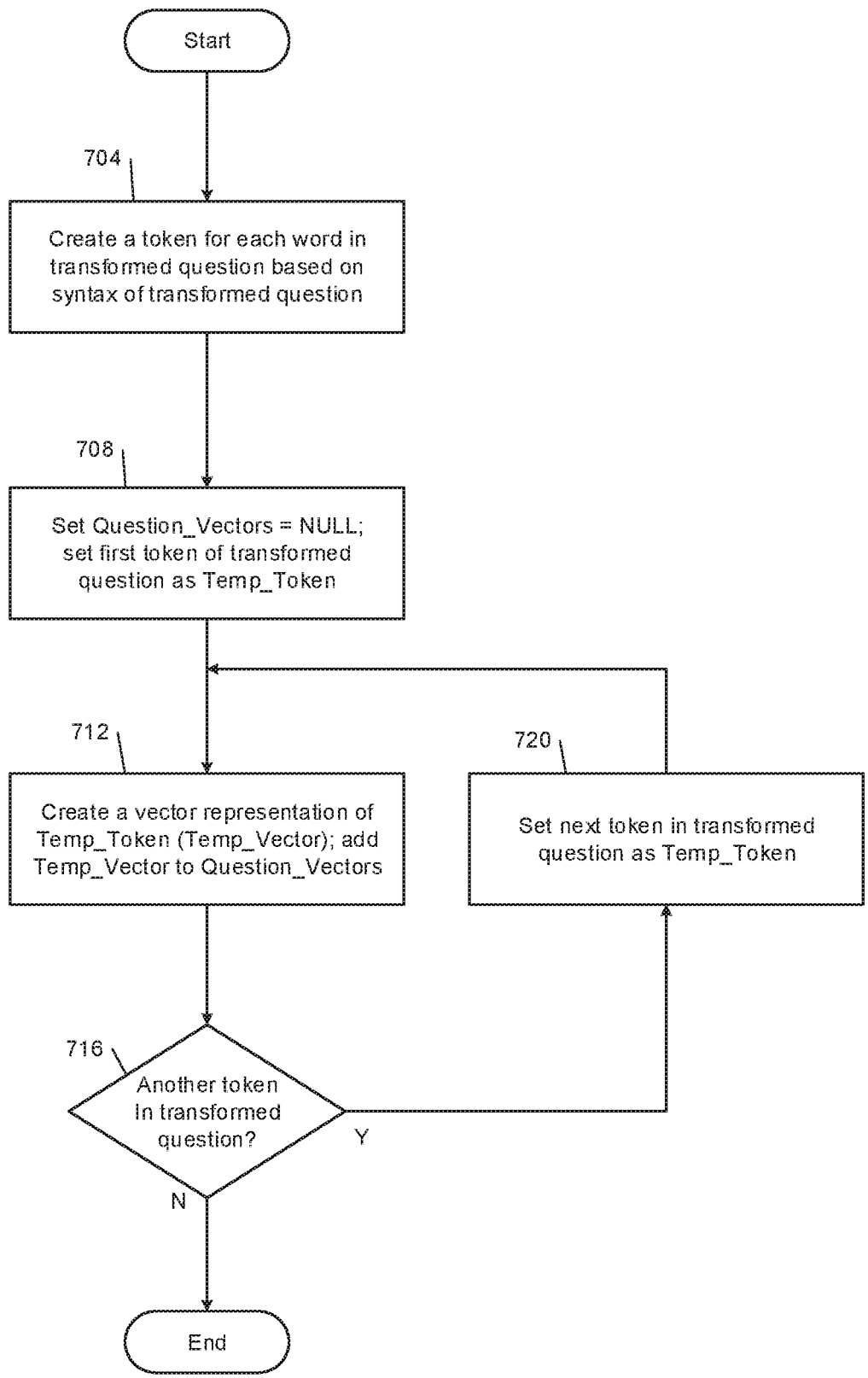
FIG. 7 is a flowchart of an example question parsing method.

At 512, control parses the transformed question, which may include converting the transformed question into a set of tokens. Each token may be represented as a vector. As one example only, the vector may have 400 values. In various implementations, parsing may be performed as shown in FIG. 7.

At 516, control sets a distance matrix (Distance_Matrix) entry associated with the received question to a null value. Distance_Matrix may track the determined distance between each pair of questions in a question repository, such as the question repository 428 of FIG. 4. The diagonal elements of Distance_Matrix may indicate distance from one question to itself and will therefore be zero.

Figure 8:
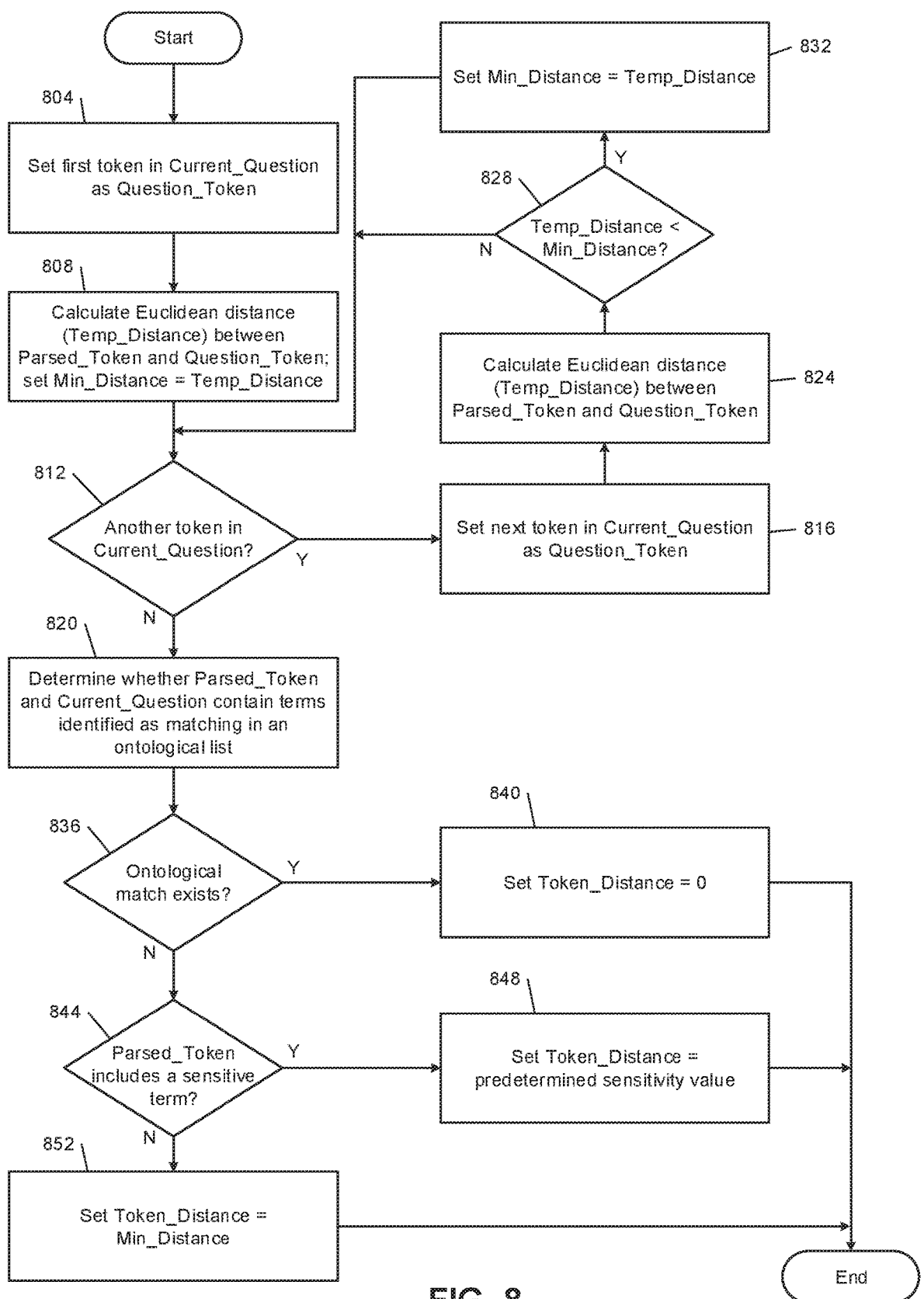
FIG. 8 is a flowchart of an example distance calculation method.

At 520, control sets the parsed question stored in the question repository as the current question (Current_Question). At 524, control sets the first token of the parsed question as Parsed_Token. Control also initializes Current_Distance to zero. Control continues at 528, where control calculates a distance (referred to as Token_Distance) associated with Parsed_Token and Current_Question. For example, distance calculation may be performed as shown in FIG. 8. At 532, control increases Current_Distance by the value of Token_Distance.

At 536, control determines whether another token is present in the parsed question. If so, control transfers to 540; otherwise, control transfers to 544. At 540, control sets the next token in the parsed question as Parsed_Token. Control then returns to 528.

At 544, control incorporates Current_Distance into Distance_Matrix to indicate the distance between the parsed question and Current_Question. Control continues at 548. At 548, if another question is stored in the question repository, control transfers to 552; otherwise, control transfers to 556. At 552, control sets the next question stored in the question repository as Current_Question. Control then continues at 524 to process the distance between the parsed question and the newly selected Current_Question.

Figure 9:
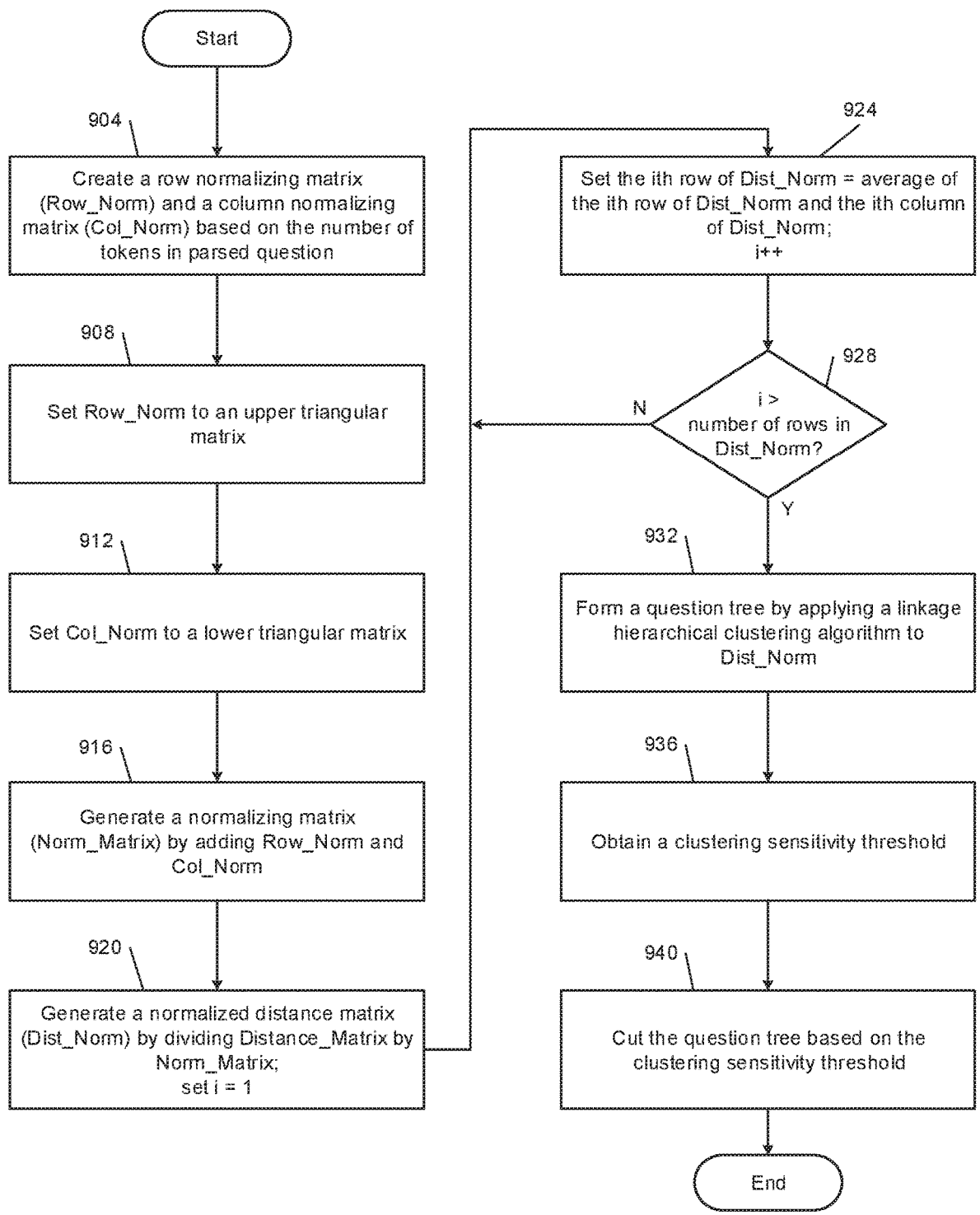
FIG. 9 is a flowchart of an example cluster analysis method.

At 556, control performs a cluster analysis on Distance_Matrix. For example, the cluster analysis may be performed as shown in FIG. 9. Control continues at 560, where control outputs results of the cluster analysis. For example, results may be provided back to the developer portal 416 by the feedback module 464 of FIG. 4.

In FIG. 6, preprocessing of a question begins at 604. Control removes nonessential words from a received question based on a predetermined word list. For example, standard stop words such as definite and indefinite articles and conjunctions may be removed. At 608, control standardizes text of the received question. For example, control may remove special characters from the question and expand contractions. In addition, control may perform word stemming, such as removing plurals to create singular nouns and conjugating verbs in a standardized tense, such as present tense.

At 612, control removes and/or replaces medical terms from the received question. For example, medical terms may include drug names. In some implementations, drug names are removed altogether. In other implementations, drug names may be replaced with a placeholder, such as Prescribed Drug. At 616, control removes punctuation from received question. Control then ends.

In FIG. 7, parsing of a question begins at 704. Control creates a token for each word in the transformed question based on the syntax of the transformed question. At 708, a set of vectors (referred to as Question_Vectors) is initialized to a null value. Control also sets the first token of the transformed question as a variable called Temp_Token.

At 712, control creates a vector representation of Temp_Token and is referred to as Temp_Vector. Control then incorporates Temp_Vector into Question_Vectors. At 716, control determines whether there is another token in the transformed question. If so, control transfers to 720; otherwise, control ends. At 720, control sets Temp_Token to be the next token in the transformed question. Control then returns to 712.

In FIG. 8, distance calculation begins at 804. Control sets the first token in the selected Current_Question as Question_Token. At 808, control calculates a distance parameter between Parsed_Token and Question_Token. This distance value is referred to as Temp_Distance. Control also initializes a variable called Min_Distance to the value of Temp_Distance. The distance value may be based on Euclidean distance between the vector representation of Parsed_Token and the vector representation of Question_Token.

At 812, control determines whether there is another token in Current_Question. If so, control transfers to 816; otherwise, control transfers to 820. At 816, control sets the next token in Current_Question as Question_Token. Control continues at 824, where control calculates a distance value between Parsed_Token and Question_Token. This distance is stored in the Temp_Distance variable.

At 828, control determines whether Temp_Distance is less than Min_Distance. If so, control transfers to 832; otherwise, control transfers to 812. At 832, control replaces the existing Min_Distance with the lower value of Temp_Distance. Control then continues at 812.

At 820, control determines whether Parsed_Token and Current_Question contain terms identified as matching in an ontological list. At 836, if an ontological match exists, control transfers to 840; otherwise, control transfers to 844. At 844, because of the ontological match, the distance between Parsed_Token and Current_Question is assumed to be zero. Control sets a value of Token_Distance to zero and ends, returning the value of Token_Distance to the process that called the distance calculation of FIG. 8.

At 844, control determines whether Parsed_Token includes a sensitive term. If so, control transfers to 848; otherwise, control transfers to 852. Sensitive terms may be those terms that are similar or identical either semantically or linguistically but have different medical meanings. Because identifying the correct medical meaning may not be reliable, the presence of a sensitive term may cause the distance between Parsed_Token and Current_Question to be set to a predetermined value. Therefore, at 848, control sets Token_Distance to a predetermined sensitivity value and ends, returning that value of Token_Distance to the calling process.

At 852, control sets Min_Distance as the Token_Distance and ends, returning the value of Min_Distance to the calling process.

In FIG. 9, cluster analysis begins at 904. Control creates a row normalizing matrix (referred to as Row_Norm) and a column normalizing matrix (referred to as Col_Norm) based on a number of tokens in the parsed question. At 908, control sets Row_Norm to be an upper triangular matrix. At 912, control sets Col_Norm to be a lower triangular matrix. At 916, control generates a normalizing matrix (referred to as Norm_Matrix) by adding Row_Norm and Col_Norm. At 920, control generates a normalized distance matrix (referred to as Dist_Norm) by dividing Distance_Matrix by Norm_Matrix. Control also initializes a counter variable named i to the value one.

At 924, control sets the ith row of Dist_Norm based on the average of the ith row of Dist_Norm and the ith column of Dist_Norm. Control then increments the value of i. At 928, control determines whether i is now greater than the number of rows in Dist_Norm. If so, control proceeds to 932; otherwise, control returns to 924.

At 932, control forms a question tree by applying a linkage hierarchical clustering algorithm to Dist_Norm. At 936, control obtains a clustering sensitivity threshold, which may be a value manually set and adjusted by an administrator. This value indicates how lax the clustering can be. The lower the threshold for similarity, the more clusters will be generated. At 940, control cuts the question tree based on the clustering sensitivity threshold. Control then ends.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. An interrogatory development system comprising:
at least one processor; and
a memory coupled to the at least one processor,
wherein the memory stores:
a question repository that includes a plurality of questions corresponding to a plurality of decision trees, wherein each of the plurality of questions corresponds to a set of the plurality of decision trees;
a distance matrix that encodes a distance between each pair of questions in the plurality of questions; and
instructions that, upon execution, cause the at least one processor to, in response to receiving a request for a new question:
convert the new question into a set of tokens;
for each question of the plurality of questions, determine a distance between the question and the new question by:
for each token of the new question, determining a minimum distance between the token and tokens of the question; and
summing the minimum distances to calculate the distance;
perform cluster analysis on the distance matrix, wherein performing cluster analysis includes (i) normalizing the distance matrix and (ii) applying a hierarchical clustering process to the normalized distance matrix;
in response to the cluster analysis indicating the new question clusters with at least one of the plurality of questions, generate an alternative question proposal and transmit the alternative question proposal as a response to the request; and
in response to the cluster analysis indicating the new question clusters with zero of the plurality of questions, add the new question to the plurality of questions and transmitting a question added message as the response to the request.

2. The interrogatory development system of claim 1 wherein the alternative question proposal is generated based on a selected question of the at least one of the plurality of questions.

3. The interrogatory development system of claim 2 wherein the instructions, upon execution, cause the at least one processor to assign ranks to the at least one of the plurality of questions and choose a highest-rank one of the at least one of the plurality of questions as the selected question.

4. The interrogatory development system of claim 3 wherein:
the ranks are based on empirical data gathered on the at least one of the plurality of questions and
the empirical data indicates how frequently data can be automatically obtained for each of the at least one of the plurality of questions.

5. The interrogatory development system of claim 4 wherein the empirical data indicates how frequently automatically obtained data for each of the at least one of the plurality of questions must be modified.

6. The interrogatory development system of claim 1 wherein the instructions, upon execution, cause the at least one processor to incorporate the distances between the questions and the new question into the distance matrix.

7. The interrogatory development system of claim 1 wherein:
- determining a first minimum distance between a first token and tokens of the question includes determining a set of distances and selecting a smallest one of the set of distances as the first minimum distance and
- each distance of the set of distances indicates distance between a vector representation of the first token and a vector representation of a respective token of the question.

8. The interrogatory development system of claim 7 wherein a distance between the vector representation of the first token and a vector representation of a second token is calculated as a Euclidean distance between the vector representation of the first token and the vector representation of the second token.

9. The interrogatory development system of claim 1 wherein:
- the memory stores a vector data store including a plurality of vector representations and
- each vector representation of the plurality of vector representations corresponds to a respective token.

10. The interrogatory development system of claim 1 wherein converting the new question into a set of tokens includes:
- performing word stemming on words in the new question;
- removing punctuation from the new question; and
- selectively removing words from the new question,
- wherein each token of the set of tokens corresponds to a remaining word of the new question.

11. The interrogatory development system of claim 10 wherein:
- a word list specifies words to be removed from the new question and
- the word list includes medical terms.

12. The interrogatory development system of claim 11 wherein the medical terms includes brand names of prescription drugs and generic names of prescription drugs.

13. The interrogatory development system of claim 1 wherein the hierarchical clustering process includes k-means clustering.

14. A method comprising:
- maintaining a question repository that includes a plurality of questions corresponding to a plurality of decision trees, wherein each of the plurality of questions corresponds to a set of the plurality of decision trees;
- maintaining a distance matrix that encodes a distance between each pair of questions in the plurality of questions; and
- in response to receiving a request for a new question:
  - converting the new question into a set of tokens;
  - for each question of the plurality of questions, determining a distance between the question and the new question by:
    - for each token of the new question, determining a minimum distance between the token and tokens of the question; and
    - summing the minimum distances to calculate the distance;
  - performing cluster analysis on the distance matrix, wherein performing cluster analysis includes (i) normalizing the distance matrix and (ii) applying a hierarchical clustering process to the normalized distance matrix;
  - in response to the cluster analysis indicating the new question clusters with at least one of the plurality of questions, generating an alternative question proposal and transmitting the alternative question proposal as a response to the request; and
  - in response to the cluster analysis indicating the new question clusters with zero of the plurality of questions, adding the new question to the plurality of questions and transmitting a question added message as the response to the request.

15. The method of claim 14 wherein the alternative question proposal is generated based on a selected question of the at least one of the plurality of questions.

16. The method of claim 15 further comprising:
- assigning ranks to the at least one of the plurality of questions and
- choosing a highest-rank one of the at least one of the plurality of questions as the selected question.

17. The method of claim 16 wherein:
- the ranks are based on empirical data gathered on the at least one of the plurality of questions;
- the empirical data indicates how frequently data can be automatically obtained for each of the at least one of the plurality of questions; and
- the empirical data indicates how frequently automatically obtained data for each of the at least one of the plurality of questions must be modified.

18. The method of claim 14 further comprising incorporating the distances between the questions and the new question into the distance matrix.

19. The method of claim 14 wherein:
- determining a first minimum distance between a first token and tokens of the question includes determining a set of distances and selecting a smallest one of the set of distances as the first minimum distance and
- each distance of the set of distances indicates Euclidean distance between a vector representation of the first token and a vector representation of a respective token of the question.

20. The method of claim 14 wherein converting the new question into a set of tokens includes:
- performing word stemming on words in the new question;
- removing punctuation from the new question; and
- selectively removing words from the new question,
- wherein each token of the set of tokens corresponds to a remaining word of the new question.

\* \* \* \* \*